US006365341B1

(12) United States Patent
Wu et al.

(10) Patent No.: US 6,365,341 B1
(45) Date of Patent: Apr. 2, 2002

(54) STABILIZATION OF HIGHLY SENSITIVE NUCLEIC ACID STAINS IN AQUEOUS SOLUTIONS

(75) Inventors: Minjie Wu, Thomaston; Hugh W. White, Camden, both of ME (US); Noriko Kusukawa, Salt Lake City, UT (US); Thomas M. Stein, Myersville, MD (US)

(73) Assignee: BioWhittaker Molecular Applications, Inc., Rockland, ME (US)

( * ) Notice: Subject to any disclaimer, the term of this patent is extended or adjusted under 35 U.S.C. 154(b) by 0 days.

(21) Appl. No.: 09/535,129

(22) Filed: Mar. 24, 2000

(51) Int. Cl.⁷ .............................. C12Q 1/00; C12Q 1/68
(52) U.S. Cl. ...................... 435/4; 435/6; 514/2; 536/22
(58) Field of Search ............................. 435/4, 6; 514/2; 536/22

(56) References Cited

U.S. PATENT DOCUMENTS 5,436,134 A     7/1995   Haugland et al. ............... 435/4
5,658,751 A     8/1997   Yue et al. ........................ 435/4
5,863,753 A     1/1999   Haugland et al. ............... 435/4

OTHER PUBLICATIONS

Clark et al., "Multiplex dsDNA Fragment Sizing Using Dimeric Intercalation Dyes and Capillary Array Electrophoresis: Ionic Effects on the Stability and Electrophoretic Mobility of DNA—Dye Complexes," Anal. Chem., vol. 69, pp. 1355–1363 (1997).

Zhaoxian et al., "Improved Stability and Electrophoretic Properties of Preformed Fluorescent Cationic Dye—DNA Complexes in a Taps—Tetrapentylammonium Buffer in Agarose Slab Gels," Analytical Biochem. vol. 252 pp. 110–114 (1997).

Primary Examiner—Louise N. Leary
(74) Attorney, Agent, or Firm—Ratner & Prestia

(57) ABSTRACT

The present invention discloses the use of quaternary compounds as stabilizing agents for highly-sensitive fluorescent nucleic acid stains in aqueous solvents, their use in gels to give increased usable shelf life, and in compositions of solvents, providing ready-to-use stain solutions.

21 Claims, No Drawings

STABILIZATION OF HIGHLY SENSITIVE NUCLEIC ACID STAINS IN AQUEOUS SOLUTIONS

FIELD OF INVENTION

This invention relates to the use of quaternary compounds to stabilize highly-sensitive fluorescent nucleic acid stains in aqueous solvents. This invention also relates to a novel composition for prestained precast agarose electrophoresis gels with increased usable shelf life for high-sensitive nucleic acid detection. This invention further relates to compositions of solvents that are useful as ready-to-use stain solutions.

BACKGROUND

Fluorescent dyes are widely used for the detection of nucleic acids in biological assays. In particular, a variety of unsymmetrical cyanine dyes have been shown to be highly sensitive and useful in electrophoresis and other solution-based assays for DNA and RNA analysis and detection. Commercial products such as SYBR® Green I and II stains (Molecular Probes Inc, Eugene OR; U.S. Pat. Nos. 5,436,134 and 5,658,751); GelStar™ stain (BioWhittaker Molecular Applications Inc, Rockland ME, U.S. Pat. No. 5,863,753); and SYBR Gold stain (Molecular Probes, Eugene OR) are some examples of those unsymmetrical cyanine dyes. These dyes provide high sensitivity due to a combination of over 1000-fold fluorescence enhancement upon binding to nucleic acids and very low background in the unbound state. The use of these dyes in ultraviolet trans-illumination enables detection of DNA at picogram levels. The mode of binding of the dyes to nucleic acids is believed to be of a different mechanism than of the more conventional phenanthridinium intercalator dyes such as ethidium bromide and propidium iodide.

Despite the superior sensitivity of unsymmetrical cyanine dyes, these dyes are not stable in aqueous solvents. They are stable in organic solvents such as dimethyl sulfoxide, but must be transferred into aqueous solvents prior to use in biological assays. In aqueous solvents, the sensitivity of these dyes for DNA detection drops to about half within 4 to 14 days of room temperature storage. As a result, precast electrophoresis gels that are prestained with these sensitive stains have a short shelf-life and are not reliably useful, even though precast gels prestained with ethidium bromide are commercially available (e.g. Reliant® precast gels, sold by BioWhittaker Molecular Applications). Thus, the availability of precast gels with highly sensitive stains is of substantial benefit, especially to high-throughput laboratories, where the large numbers of samples would otherwise necessitate the casting of numerous gels.

Detergents have been used to improve the stability of highly sensitive nucleic acid stains but only marginally prolong the stability of stains, if at all (see Example 1, Table 1), and are not useful for precast gels. Reports from Mathies (Zeng et al 1997, *Analytical Biochemistry* 252:110–114; Clark et al 1997, *Analytical Chemistry* 69: 1355–1363) describe the use of tetrapentylammonium ion in TAPS (3-[tris-(hydroxymethyl)methylamino]-1-propanesulfonic acid) buffer to increase the stability of complexes formed between DNA and bisintercalator dyes. However, these reports do not suggest that the stability of the dyes themselves were effected, or mention the effect on unsymmetrical cyanine dyes such as SYBR Green and GelStar stains. Therefore, there is still a need for a method to stabilize highly sensitive nucleic acid stains, and to provide a means of creating prestained, precast gels and solutions with a useful shelf life.

BRIEF SUMMARY OF THE INVENTION

The present invention provides a method for stabilizing highly sensitive fluorescent nucleic acid stains in aqueous solvents by adding one or more quaternary compounds to the solvent. It is also an object of this invention to provide an electrophoresis gel composition for a precast electrophoresis gel system which includes a gel, an electrophoresis buffer, a highly sensitive fluorescent nucleic-acid binding dye, and one or more quaternary compounds, said quaternary compounds causing the dyes incorporated into the gel to have increased stability in aqueous solvents. It is further an object of this invention to provide a stabilized stain solution comprising an aqueous solvent, a fluorescent nucleic acid stain, and a stabilizing amount of one or more quaternary compounds. The quaternary compounds of the invention have the general structural formula $R_4NX$ where $R_4N$ is a cation and each R is independently a $C_{1-6}$ alkyl group or a $C_{1-6}$ alkoxy group, N is nitrogen, X is a halide anion or a hydroxy anion which dissociates from the cation $(R_4N)^+$ in an aqueous environment; and wherein the highly sensitive fluorescent nucleic acid stain comprises a cyanine dye. The above objects and advantages of the present invention will be apparent upon consideration of the following detailed description.

DETAILED DESCRIPTION OF THE INVENTION, AND THE PREFERRED EMBODIMENT

We provide a method of extending the useful shelf life of fluorescent stains in aqueous solution, by adding one or more quaternary compounds to the aqueous solvent containing the stain. The quaternary compound has a structural formula $R_4NX^-$ where $R_4$ consists of four homogeneous or heterogeneous $C_{1-6}$ alkyl or alkoxyl chains that are covalently linked to a quaternary nitrogen, N; and X is an anion which will dissociate from the cation $(R_4N)^+$ in an aqueous environment. In preferred embodiments, $X^{31}$ is a halide or hydroxyl anion. In more preferred embodiments, $X^-$ is a chloride or a bromide ion. The quaternary compound is readily dissolved in the aqueous system and may be present in any effective amount. In general, the quaternary compound is present at concentrations between 1 mM and 200 mM, which can be optimized according to use. When used in gels for electrophoretic separation of nucleic acids and proteins, the useful concentration of the quaternary compound is between 5 and 20 mM.

Fluorescent stains are widely used for the detection of biological molecules. One such group is the unsymmetrical cyanines that fluoresce upon binding to nucleic acids, including but not limited to compounds such as SYBR Green I and II, SYBR Gold, and GelStar nucleic acid stains, and their derivatives, and other stains described in U.S. Pat. No. 5,436,134, U.S. Pat. No. 5,658,751, and U.S. Pat. No. 5,863,753. When these stains are in aqueous systems (such as electrophoresis gels or biological buffers) and in the presence of the aforementioned quaternary compounds, there is at least a 4-fold increase in the half-life of these stains. For purposes of the present invention, half-life, or t½ is defined as the time it takes for the stains to lose half of their fluorescence intensity that results from DNA binding. Quaternary salts of tetramethylammonium, tetrabutylammonium, and tetrapentylammonium are particularly preferred embodiments. Quaternary ammonium hydroxides are conveniently used as part of the buffer system (such as in the case of TAPS buffer) and are particularly compatible with high-resolution gel electrophoresis. Quaternary ammonium halides can be conveniently used to supplement buffered or non-buffered solvents for storage of stains. A combination of two or more quaternary compounds can be used as long as it is compatible with the use. Quaternary ammonium compounds with carbon chains larger than 6, such as but not limited to tetrahexylammonium compounds (which are not soluble in the aqueous solvents) and detergents (see Table I), are not useful for purposes of the present invention. However, detergents may be used in addition to the inventive quaternary compounds to further enhance the stain-stabilizing effect. An example is shown in Table 3, where the addition of detergent to a solution containing tetramethylammonium hydroxide extends the half-life of SYBR Green I stain by 1.6 to 2-fold in addition to the 4-fold increase already achieved by tetramethylammonium hydroxide alone.

Further to the aforementioned unsymmetrical cyanines, fluorescent nucleic acid dyes such as cyanine dimers and monomers may also be stabilized by the quaternary compounds, whereas conventional phenanthridinium nucleic acid dyes such as ethidium bromide and propidium iodide are not. Preferred cyanine dimers and monomers include but are not limited to TOTO, YOYO, TO-PRO (each commercially available from Molecular Probes, Inc., Eugene, OR), and Cy3, Cy5, and Cy7 (each commercially available from Amersham Life Science Inc., Arlington Heights, Ill).

The electrophoresis gel of the invention comprises a hydrogel, a buffer system, a fluorescent nucleic acid dye, and one or more quaternary compounds. Hydrogels useful for electrophoresis include agarose and polyacrylamide gels, although when polyacrylamide gels are used, the stain may need to be incorporated after gel formation to avoid breakdown of stain during acrylamide polymerization. Buffers normally used for electrophoresis including but not limited to MOPS, TAPS (each commercially available from Sigma, St. Louis, Mo.), TAE (1×concentration is 40 mM Tris-acetate, 1 mM EDTA), and TBE can be used for the invention, provided that the pH of the buffers are appropriately adjusted after addition of the quaternary compounds and that the system is compatible with electrophoretic separation. The combination of TAPS buffer and tetrapentylammonium hydroxide is particularly preferred. The combination of TAPS buffer and tetrapentylammonium hydroxide and tetrabutylammonium hydroxide is preferred. The combination of TBE or TAE buffers with tetrapentylammonium bromide is also preferred. Fluorescent nucleic acid dyes can be unsymmetrical cyanine stains. The use of GelStar nucleic acid stain is particularly preferred. The use of SYBR Green, or SYBR Gold stain gels requires optimization of the stain concentration and the amount of DNA or RNA applied to the gel in order to obtain high-resolution electrophoresis results.

Shelf-stable dye solutions of the invention are comprised of a fluorescent cyanine dye, an aqueous solvent, and one or more quaternary compounds. The solutions may be used to stain gels after electrophoresis in order to visualize nucleic acids or proteins that were separated on the gels.

EXAMPLE 1

Dye Stabilization in Gels

SeaKem LE agarose gels (1% w/v, BMA Inc) were cast in 1×TAPS buffer (3-(N-tris(hydroxymethyl)methylamino)- propanesulfonic acid, 40 mM) in the presence of 1×GelStar nucleic acid stain (BMA Inc) and additives indicated in Table 1. Gels were incubated in the dark for 6 days at 45° C., and tested for the detection of DNA as follows: Gels were submerged in 1×TAPS electrophoresis buffer without dye. Then DNA was electrophoresed through the gel at 20 V/cm for one hour. The intensity of a 2.5 ng DNA band was examined by transillumination at 300 nm. The stain in the gel was considered stabilized if the fluorescence intensity of the DNA was more than 80% compared to when the gel was freshly prepared with stain. GelStar nucleic acid stain was stabilized by the presence of tetrapentylammonium and tetrabutylammonium compounds, but not with quaternary ammonium detergents. The quality of DNA resolution in fresh gels were recorded as "Good" when the DNA band was sharp, "Fair" when the DNA band was broad, and "Poor" when the DNA band was fuzzy.

TABLE 1

The effect of additives on the stability of GelStar nucleic acid stain in gels

|  | Additive | Concentration | Resolution when fresh | Dye stabilization at 45° C. |
|---|---|---|---|---|
| Control | Sodium hydroxide (NaOH) | Titrated the buffer to pH 8.2 | Fair | No |
| Invention | Tetrapentylammonium hydroxide (TPAOH) | 7.3 mM | Fair | Yes |
| Invention | TPAOH | 14.6 mM | Good | Yes |
| Invention | Tetrabutylammonium hydroxide (TBAOH) | 14.6 mM | Fair | Yes |
| Invention | TPAOH and TBAOH | 7.3 mM each | Good | Yes |
| Invention | NaOH and tetrapentylammonium bromide (TPABr) | NaOH added to titrate TAPS to pH 8.2, TPABr was 14.6 mM | Fair | Yes |
| Non-operative | Tween-20 | 0.1% (v/v) | Fair | No |
| Non-operative | Dodecyltrimethylammonium bromide | 28 mM | Poor | No |
| Non-operative | Hexadecyltrimethylammonium bromide | 2 mM | Poor | No |

EXAMPLE 2

Dye Stabilization in Solution

SYBR Green I nucleic acid stain (1×, BMA Inc) was suspended in the solvents indicated (Table 2) and kept in polypropylene bottles at 21–23° C. under ambient light. TBE buffer at 1×strength consisted of 89 mM Tris, 89 mM boric acid, and 2 mM EDTA. Periodically, 5 μl of the solutions were mixed with 3 ng of lambda DNA, and then spotted onto a polystyrene Petri Dish (VWR, Massachusetts). The spot was excited at 500 nm (Dark Reader, Clare Chemical Research, Colorado) and the fluorescence intensity was captured and integrated over a constant surface area by the AlphaImager ("Spot Density Tools", Alpha Innotech, California). The numbers were then normalized against the intensity at time zero. The time it took the stain to lose half of its fluorescence intensity was recorded as t½. The t½ of SYBR Green I nucleic acid stain without inventive additives was between 5 and 14 days, depending on the type of control solvent.

TABLE 2

Solvents

| Solvent | | Composition | t½ of SYBR Green I stain in solvent |
|---|---|---|---|
| A | Control | 1xTAPS buffer, titrated with 1N NaOH to pH 8.2 at 25° C. | 5 days |
| B | Invention | 1xTAPS buffer, 14 6 mM TPAOH (pH 8.2 at 25° C.) | 92 days |
| C | Invention | 1xTAPS buffer, 7.3 mM TPAOH (pH 8.2 at 25° C.) | 92 days |
| D | Invention | Solvent A with 1.5 mM TPABr | 24 days |
| E | Invention | Solvent A with 3.6 mM TPABr | 25 days |
| F | Invention | Solvent A with 7.3 mM TPABr | >100 days |
| G | Invention | Solvent A with 14.6 mM TPABr | >100 days |
| H | Invention | Solvent A with 29.2 mM TPABr | >100 days |
| I | Invention | Solvent A with 58.4 mM TPABr | >100 days |
| J | Invention | Solvent A with 116.8 mM TPABr | >100 days |
| K | Control | 1x TBE buffer (pH 8.0) | 5 days |
| L | Invention | Solvent K with 14.6 mM TPABr | 67 days |
| M | Control | Water (pH 6.8) | 14 days |
| N | Invention | Solvent M with 14.6 mM TPABr (pH 5.0) | >100 days |

EXAMPLE 3

Dyes that are Stabilized by the Additive

Unsymmetrical cyanines (1xSYBR Green I, 1xSYBR Gold, and 1xGelStar nucleic acid stains), Hoechst 33258 pentahydrate (bis-benzimide: BisBnz, 1.5 ug/ml) and phenanthridine intercalator dyes (1 μg/ml ethidium bromide; 10 μg/ml propidium iodide) were tested for their response to the stabilizing agent TPABr. Dyes were tested in 1xTAPS buffer that was adjusted with NaOH to pH 8.2, with or without 14.6 mM TPABr. Dye stabilization was measured using the method described in Example 2 except that for the measurement of ethidium bromide, propidium iodide and Hoechst 33258 dyes, transillumination at 300 nm was used. The effect of TPABr on the stability of these three compounds was marginal. In contrast, the t ½ of SYBR Green was extended to over 100 days (compared to 5 days without TPABr), SYBR Gold stain to 36 days (compared to 9 days without TPABr); and GelStar stain to 24 days (compared to 4 days without TPABr).

EXAMPLE 4

Effect of Detergents on Dye Stabilization

SYBR Green I nucleic acid stain (1x) was suspended in 1xTAPS buffer with the additives indicated (Table 3) and tested whether it will be stabilized using the method described in Example 2.

TABLE 3

The effect of detergents in combination with quaternary salt

| Solvent | | Compound added | Concentration of detergent | t½ of SYBR Green I stain |
|---|---|---|---|---|
| A | Control | NaOH, pH 8.2 | 0% | 5 days |
| O | Invention | 14.6 mM Tetramethylammonium hydroxide (TMAOH), pH 8.2 | 0% | 20 days |
| P | Invention | Solvent O with Tween-20 | 0.04% (v/v) | 40 days |
| Q | Invention | Solvent O with sodium dodecyl sulfate | 0.05% (w/v) | 32 days |
| R | Invention | Solvent O with polyoxyethylene 5 octyl ether | 1.39% (v/v) | 38 days |

We claim:

1. A method to stabilize a highly sensitive fluorescent nucleic acid stain in aqueous solvents comprising adding one or more quaternary compounds to the solvent, wherein
the quaternary compound has a structural formula of $R_4NX$, where $R_4N$ is a cation and each R is independently a $C_{1-6}$ alkyl group or a $C_{1-6}$ alkoxy group;
N is nitrogen;
X is a halide anion or a hydroxy anion which dissociates from the cation $(R_4N)^+$ in an aqueous environment; and
wherein the highly sensitive fluorescent nucleic acid stain comprises a cyanine dye.

2. The method of claim 1 wherein said quaternary compound is present in a concentration in the range of 1 mM and 200 mM.

3. The method of claim 1 wherein said quaternary compound is present in a concentration in the range of 5 mM and 2 mM.

4. The method of claim 1 wherein the quaternary compound comprises a tetrapentylammonium salt, a tetrabutylammonium salt, or a mixture of tetrapentylammonium salt and tetrabutylammonium salt.

5. The method of claim 1 wherein the quaternary compound comprises tetrapentylammonium bromide, tetrapentylammonium chloride, or tetrapentylammonium hydroxide.

6. The method of claim 1 wherein the cyanine dye comprises an unsymmetrical cyanine dye.

7. The method according to claim 1 wherein the highly sensitive fluorescent nucleic acid stain comprises SYBR Green I, SYBR Green II, GelStar, and SYBR Gold stains, or a derivative thereof.

8. An electrophoresis gel composition comprising a gel, an electrophoresis buffer, a highly sensitive fluorescent nucleic acid stain, and a stabilizing amount of one or more quaternary compounds wherein the quaternary compound has a structural formula of $R_4NX$,
where $R_4N$ is a cation and each R independently comprises a $C_{1-6}$ alkyl group or a $C_{1-6}$ alkoxy group;
where N is nitrogen;
where X is a halide anion or a hydroxy anion which dissociates from the cation $(R_4N)^+$ in an aqueous environment; and
where the highly sensitive fluorescent nucleic acid stain comprises a cyanine dye.

9. The composition of claim 8 wherein said quaternary compound is present in a concentration in the range of 1 mM and 200 mM.

10. The composition of claim 8 wherein said quaternary compound is present in a concentration in the range of 5 mM and 20 mM.

11. The composition of claim 8 wherein the quaternary compound comprises a tetrapentylammonium salt, a tetrabutylammonium salt, or a mixture of tetrapentylammonium salt and tetrabutylammonium salt.

12. The composition of claim 8 wherein the cyanine dye comprises an unsymmetrical cyanine dye.

13. The composition of claim 8 wherein the highly sensitive fluorescent nucleic acid stain comprises SYBR Green I, SYBR Green II, GelStar, and SYBR Gold stains, or a derivative thereof.

14. The composition of claim 8 wherein the gel comprises agarose, the stain is GelStar; and the quaternary compound comprises tetrapentylammonium hydroxide, tetrapentylammonium bromide, or a combination of tetrapentylammonium hydroxide and tetrabutylammonium hydroxide.

15. The composition of claim 8 wherein the gel comprises agarose and the stain is SYBR Green I.

16. A stabilized stain solution comprising an aqueous solvent, a fluorescent nucleic acid stain, and a stabilizing amount of one or more quaternary compounds, wherein said quaternary compound has a structural formula of $R_4NX$, where $R_4N$ is a cation and each R independently comprises a $C_{1-6}$ alkyl group or a $C_{1-6}$ alkoxy group;

where N is nitrogen;

where X is a halide anion or a hydroxy anion which dissociates from the cation $(R_4N)^+$ in an aqueous environment; and where the fluorescent nucleic acid stain comprises a cyanine dye.

17. The stain solution of claim 16 wherein said quaternary compound is present in a concentration in the range of 1 mM and 200 mM.

18. The stain solution of claim 16 wherein said quaternary compound is present in a concentration in the range of 5 mM and 20 mM.

19. The stain solution of claim 16 wherein the quaternary compound comprises either tetrapentylammonium salt, a tetrabutylammonium salt, or a mixture of tetrapentylammonium salt and tetrabutylammonium salt.

20. The stain solution of claim 16 wherein the cyanine dye comprises an unsymmetrical cyanine dye.

21. The stain solution of claim 16 wherein the fluorescent nucleic acid stain comprises SYBR Green I, SYBR Green II, GelStar, and SYBR Gold stains, or a derivative thereof.

* * * * *

UNITED STATES PATENT AND TRADEMARK OFFICE
CERTIFICATE OF CORRECTION

PATENT NO. : 6,365,341 B1
DATED : April 2, 2002
INVENTOR(S) : Minjie Wu et al.

It is certified that error appears in the above-identified patent and that said Letters Patent is hereby corrected as shown below:

Column 2,
Line 39, delete "X" and insert therefor -- $X^-$ --
Line 41, delete "$X^{31}$" and insert therefor -- $X^-$ --

Signed and Sealed this

First Day of October, 2002

Attest:

Attesting Officer

JAMES E. ROGAN
Director of the United States Patent and Trademark Office